United States Patent [19]

Wolff

[11] 4,108,601
[45] Aug. 22, 1978

[54] STEAM STERILIZING APPARATUS

[75] Inventor: Robert Wolff, Mantoloking, N.J.

[73] Assignee: Better Built Machinery Corporation, Saddle Brook, N.Y.

[21] Appl. No.: 755,440

[22] Filed: Dec. 29, 1976

[51] Int. Cl.² ............................ A61L 3/00; A61L 5/00
[52] U.S. Cl. ............................................ 21/96; 21/98
[58] Field of Search ........................ 21/93, 94, 96–98

[56] References Cited

U.S. PATENT DOCUMENTS

| 3,093,449 | 6/1963 | Kotarski et al. | 21/94 |
|---|---|---|---|
| 3,454,353 | 7/1969 | Bjork | 21/94 |
| 3,482,930 | 12/1969 | Huber | 21/94 |
| 3,488,142 | 1/1970 | Cooper | 21/93 |
| 4,003,703 | 1/1977 | Montgomery et al. | 21/93 |

FOREIGN PATENT DOCUMENTS 1,153,490  8/1963  Fed. Rep. of Germany .............. 21/94

OTHER PUBLICATIONS

Perry; "Chem. Engr's. Handbook"; 3rd Ed.; 1950; pp. 1450 & 1451.

Primary Examiner—Morris O. Wolk
Assistant Examiner—Bradley R. Garris

Attorney, Agent, or Firm—Robert S. Bramson; James A. Drobile

[57] ABSTRACT

Apparatus for sterilizing laboratory and hospital glassware, liquids, instruments, garments and the like comprising a sterilizer enclosure having a steam jacket surrounding the same, a source of steam and means, connected in parallel, to supply steam to said jacket at one of two predetermined pressures, means for interconnecting said jacket and said interior of said sterilizer, and means responsive to a predetermined temperature setting for the interior of the sterilizer to selectively initiate and discontinue the supply of steam to said jacket in response to the temperature in said sterilizer. A process for sterilizing laboratory and hospital glassware, liquids, instruments, garments and the like comprising the steps of inserting the materials to be sterilized in a closed, sealed, jacketed sterilizer, introducing steam into the jacket of said sterilizer to preheat said jacket, interconnecting said jacket and the interior of said sterilizer initially to displace any air within said sterilizer; continuing to interconnect the jacket and the interior of said sterilizer; providing the jacket wth steam at one of two different predetermined pressures; sensing the temperature within said sterilizer and introducing steam into said jacket at said higher pressure in response to said temperature sensitive means to maintain a variable, predetermined temperature within said sterilizer.

5 Claims, 4 Drawing Figures

STEAM STERILIZING APPARATUS

BACKGROUND OF THE INVENTION

1. Field of the Invention

The invention relates to a sterilizing apparatus of the type utilized to sterilize hospital and laboratory glassware, liquids, instruments, parenteral solutions, and paper and fabric materials, such as surgical gowns, sheets and pillow cases, and like objects, and to a process for sterilizing such objects.

2. State of the Art

Steam sterilizers are well known and are extensively utilized in hospitals, laboratories and other facilities for the purpose of sterilizing many types of solid, liquid-containing and porous objects. Typical such sterilizers are disclosed in U.S. Pat. Nos. 3,325,042 and 3,488,142.

Steam sterilizers commonly utilize one of two systems to regulate temperature. The system 200 illustrated in FIG. 2 is referred to as a "hi-low" system, utilizing a high-low pressure regulator 214 which has two positions that regulate the pressure, such as at 15 p.s.i.g. (low) or 27 p.s.i.g. (high). These two positions are manually controlled. The low pressure steam is utilized for sterilization at about 250° F and the high pressure steam is utilized for sterilization at about 270° F. The pressure regulator 214 is manually set for either the low or high pressure and the temperature sensor 218, which is also manually set, then regulates a control valve 216 to open the regulator 214 and introduce more steam to jacket 212 if the temperature deviates from the predetermined temperature to raise the temperature of the sterilizer chamber. The disadvantage of this system is that the operator must make two adjustments (in the control valve 216 and the high-low regulator 214) when going from 250° to 270° F. Failure to do so will result in an unsatisfactory cycle. Also, with this construction, only two predetermined temperatures can be achieved. For example, if a 260° F cycle is desired, the high-low valve 214 must be set on high and the jacket temperature would reach 270°, resulting in superheated steam in the sterilizing chamber.

Another prior art construction 220 is illustrated in FIG. 3. In this construction the low pressure 228 regulator is set, for example, at 15 p.s.i.g. and the high pressure regulator 232 is set, for example, at 35 p.s.i.g. The jacket pressure is established by opening either one of two solenoid valves 226 (for low pressure steam) or 230 (for higher pressure steam). Additional regulators and solenoid valves can be added to give a wider range of pressures and consequent sterilizing temperatures. The temperature sensor 234 regulates the chamber control valve 224, to regulate the introduction of a suitable quantity of steam into the chamber of sterilizer 230, depending upon the predetermined setting and the pressure of the jacket steam. The disadvantages of this apparatus and process are similar to those of the FIG. 2 apparatus in that two selections (rather than one) must be made to establish sterilizer temperature namely, the control valve operating temperature and the particular high pressure or low pressure regulator utilized to supply steam to the sterilizer. Also, this system produces only specific temperatures and cannot be varied to a great variety of temperatures merely by adjusting the temperature controller.

The systems of the prior art are inefficient, in that they require more than a single manual operation in order to achieve a predetermined temperature setting and are therefore more susceptible of error than the apparatus of this invention. The prior art devices are not capable of achieving, with minimal instrumentation, a great variety of temperatures between the temperature established by the low pressure and high pressure supply, and inefficiently use available steam by allowing, at times, the jacket pressure and temperature to be different from the pressure and temperature of the sterilizer interior. The disadvantages of the prior art are overcome by the process and apparatus of this invention.

BRIEF SUMMARY OF THE INVENTION

The apparatus of the invention comprises a sterilizer having a steam jacket surrounding the sterilizing chamber, and having a chamber valve and conduit interconnecting the jacket and the sterilizer interior. Steam from a suitable and well-known type of source is introduced to the jacket through two parallel connections for providing steam to the jacket at one of two predetermined pressures, preferably a low pressure of 15 p.s.i.g and a high-pressure in the range from about 35 to 40 p.s.i.g. A temperature sensor, of a type well known in the art, senses the temperature within the sterilizing chamber, and when the temperature varies from the predetermined setting of the controller by more than 1° (the sensitivity of the controller) the controller operates a jacket solenoid valve for introducing steam into the jacket at the higher pressure. The jacket and sterilizer interior remain in fluid communication at all times during the steam introduction portion of the sterilizing cycle, and the temperature sensor controls the flow of steam from the source through the high pressure line into the jacket. The quantity of high pressure steam introduced through the jacket into the sterilizer chamber thereby determines the temperature of the sterilizer chamber.

The temperature controller is capable of being set at any desired temperature between selected limits, usually between 212° and 270° F, and most preferably between 250° and 270° F. When the sterilizer chamber interior temperature varies from the predetermined setting of the controller, the controller opens the jacket solenoid valve for the high pressure line and introduces additional high pressure steam into the jacket, and thereby into the chamber interior (which, during the steam sterilizing portion of the cycle, is in fluid communication with the chamber interior) until the temperature in the chamber interior reaches the predetermined level established by the controller, at which time the controller automatically closes the jacket solenoid valve controlling the flowing steam through the high pressure line into the jacket.

The invention includes means for evacuating air from the sterilizer chamber prior to actual sterilization, and for evacuation of steam from the chamber after sterilization and prior to opening the sterilizer or drying the sterilizer contents.

The means for evacuating the sterilizer contents comprises either a slow bleed valve for slowly bleeding steam from the chamber and mixing it with cooling water in an ejector, or a fast exhaust, solenoid-operated valve, for permitting fast exhaustion of the steam contents of the sterilizer, also mixing the exiting steam with water from a suitable supply in an ejector to cool the steam to safe temperature, typically about 140° F.

In a preferred embodiment of the invention, when it is desired to sterilize "soft" goods, such as surgical wraps, curtains, surgical gowns, sheets, pillow cases and the like, it is sometimes desirable to use a high vacuum system attached to the sterilizer for quickly evacuating the sterilizer to "pump" air out of the porous packs in which the soft goods are obtained. The conventional method for achieving such a vacuum is by using a water ring vacuum pump, which is very expensive. The apparatus of this invention has two settings, one for low vacuum exhaust utilizing an ejector, and the other for high vacuum exhaust utilizing the ejector in combination with a high pressure (100 p.s.i.) turbine pump. A water tank is also provided so that service water can be collected and recirculated to reduce the amount of water required for this function.

In the process of this invention steam is initially supplied to the sterilizer jacket at a low pressure, preferably 15 p.s.i.g., to preheat the jacket. A high pressure line is controlled by the temperature controller, which senses temperature within the sterilizer and opens the high pressure line to introduce high pressure steam into the jacket until the predetermined temperature is reached. During the step of steam sterilization, the jacket is maintained in fluid communication with the sterilizer chamber. Therefore the temperature sensor opens the high pressure line to introduce more steam directly into the sterilizer interior through the jacket into the sterilizer chamber, whenever the temperature within the sterilizer chamber is below a predetermined temperature.

OBJECTS OF THE INVENTION

It is therefore an object of this invention to provide a sterilizer for laboratory and hospital glassware, liquids, instruments and soft goods which is capable of providing a wide variety of temperatures of steam sterilization between two predetermined limits by the use of a single temperature setting and maintaining that temperature substantially constant at all times.

Another object of this invention is to provide a steam sterilizer of the type described in which the sterilizer jacket and interior are maintained at substantially the same temperature throughout the period of steam sterilization.

Yet another object of this invention is to provide a sterilizer of the type described which achieves temperature regulation of sterilization by regulating the quantity of high pressure steam introduced into the jacket and chamber interior of the sterilizer.

Still another object of this invention is to provide a sterilizer ejector having a high vacuum and low vacuum setting, capable of achieving efficient evacuation of steam from the sterilizer in a minimum period of time, with minimum cost and maximum efficiency.

A further object of this invention is to provide a process for sterilizing laboratory and hospital apparatus of the type described, wherein the sterilizer jacket and chamber are maintained in fluid communication during steam sterilization and temperature control is achieved by opening and closing a high pressure supply line in response to a sensing of the temperature in a sterilizing chamber.

These and other objects of this invention will be readily perceived from the following detailed description of the invention, when read in connection with the appended drawings.

DETAILED DESCRIPTION OF THE INVENTION

Figure 1:
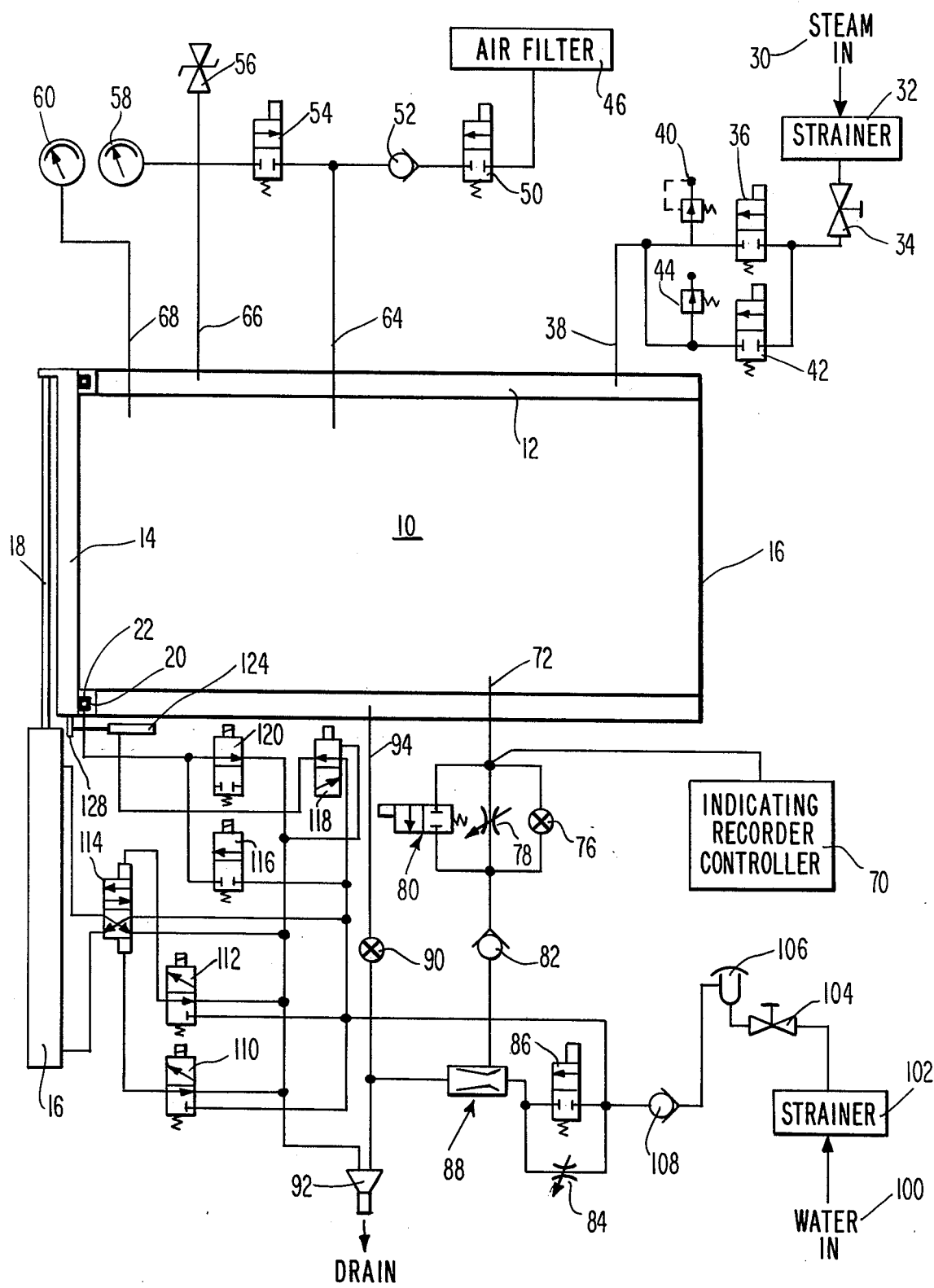
FIG. 1 is a schematic view, taken in vertical cross-section along the longitudinal axis of a sterilizer in accordance with this invention.
Figure 2:
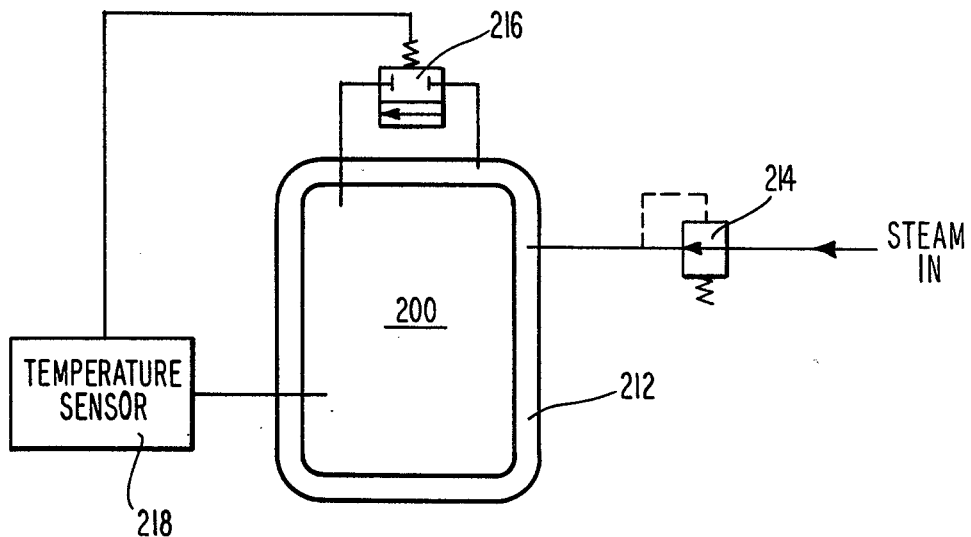
FIG. 2 is a schematic view, in vertical transverse cross-section, of a prior art apparatus for sterilizing hospital and laboratory equipment of the type described.
Figure 3:
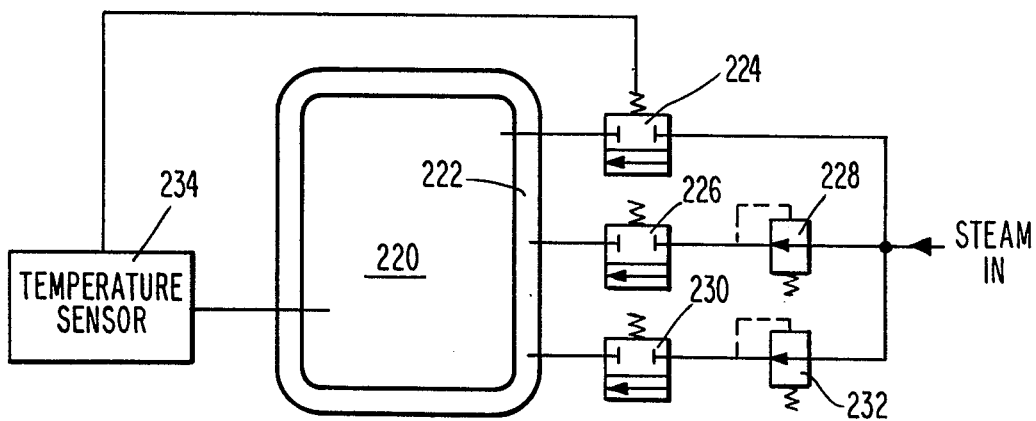
FIG. 3 is a schematic view of the type illustrated in FIG. 2, showing yet another prior art apparatus.

Viewing FIG. 1, a sterilizer of rounded rectangular cross-section (not shown, but similar to FIG. 2) is seen to comprise a sterilizer chamber 10, having a closed rear end 16 and an open front end which is closed by a vertically sliding door 14. It is to be noted that, in some models, doors can be provided at both ends. Door 14 is raised and lowered by an hydraulic cylinder 16 operating a piston 18 connected to the door. The cylinder 16 can also be pneumatically operated, if desired. The sterilizer chamber 10 is completely-surrounded about its length by a jacket 12. Steam is introduced into jacket 12 to preheat and post-heat the sterilizer and to introduce steam into the sterilizer chamber 10 during sterilization. All of the foregoing general features of the sterilizer construction are well-known in the art, and do not comprise a part of this invention.

Steam for sterilizing and drying is introduced from a suitable steam source 30, such as a boiler, and passes through a conventional strainer 32, of a type well known in the art, which removes boiler scale or any other foreign debris which may be in the steam. The steam then passes through a manual control valve 34 which is usable to close the entire steam supply system, if desired. Steam exiting from manual control valve 34 is introduced to conduit 38 into the jacket 12 of the sterilizer through one of two parallel connected conduits. The first conduit includes a heat jacket solenoid valve 36 for controlling the preheat cycle, in a manner more fully described below, and a pressure reducing valve 40, the purpose of which is to reduce the pressure in that conduit to a predetermined level, which is desirably established at 15 p.s.i.g.

The second conduit includes jacket solenoid valve 42 for controlling steam flow through the second conduit, and pressure reducing valve 44, which is set at a substantially higher pressure than reducing valve 40, for maintaining a pressure preferably in the range of about 35 to 40 p.s.i.g. in the second conduit. The pressure and amount of steam introduced through the second conduit and jacket 12 into chamber 10 determine the temperature of the sterilizer chamber.

Air is admitted into the sterilizer interior through conduit 64 which communicates with the sterilizer chamber 10 and which receives ambient air which passes through biological air filter 46. The air supply line includes air admission solenoid valve 50 to control the admission of air during predetermined intervals after completion of steam sterilizing for drying cycle, as described below, and check valve 52, the function of which is to preclude steam escaping through the filter 46. Conduit 66 is connected to jacket 12 and is in fluid communication with conduit 64 through chamber solenoid valve 54. Safety valve 56 is also connected to conduit 66 for the purpose of releasing pressure in the jacket 12 when it exceeds a predetermined safe level. Pressure gauge 60 is in fluid communication with the sterilizer interior through conduit 68 and provides a continuous reading of the pressure within the sterilizer, and pressure gauge 58 is in fluid communication with jacket 12 through conduit 66 and provides a reading of the pressure in the jacket.

In operation, the air supply solenoid valve 50 is normally closed, and is only opened at the completion of the steam sterilization cycle, when steam is being evacuated from the sterilizer unit, to replace the evacuated steam when the sterilizer contents are to be dried. If no drying is to be accomplished, the valve 50 remains closed.

Control valve 54 is an essential part of the invention, in that it permits fluid communication between the jacket 12 and sterilizer chamber 10 at all times during the steam sterilizing operation, so that the pressure and therefore the temperature in the jacket and in the sterilizer are substantially equal at all times. Unlike prior art processes which selectively control the fluid communication between the jacket 12 and the sterilizer chamber 10 during the steam sterilizing operation, in the apparatus and process of this invention fluid communication is constantly maintained between the jacket 12 and the sterilizer chamber 10 during the steam sterilizing operation.

Solenoid valve 54 is closed during pre-heating, so that there may be steam in the jacket 12, and not in the sterilizing chamber 10, during pre-heating and while the sterilizer is being loaded. Also, at the conclusion of the sterilization operation, when the sterilizer is being evacuated or when the contents of the sterilizer are about to be dried, valve 54 is closed and there is no fluid communication between the jacket 12 and the sterilizer chamber 10.

At the base of the sterilizer unit, to permit gravity (or other) evacuation of the sterilizer under appropriate circumstances, the evacuating system is desirably located. The evacuating system is in fluid communication with the sterilizer chamber 10 through conduit 72. Indicating recorder controller 70 is connected to the interior of sterilizer chamber 10 through conduit 72 for the purpose of providing a constant reading of the temperature in the sterilizer chamber 10. The indicating recorded controller records, as on circular graph paper, the temperature within the chamber 10 at all times, so that a visual record of that temperature is provided for the sterilization cycle, in order to insure that the sterilization cycle has the necessary time duration and minimum temperature to achieve complete sterilization. The indicating recorder controller 70 is connected (not shown) to jacket solenoid valve 42 which places the high pressure steam line in fluid communication with the jacket 12 when the valve 42 is opened, in order to provide the jacket 12 and (when the jacket is in fluid communication with the sterilizer chamber 10) the sterilizer chamber 10 with high pressure steam.

The indicating recorder controller 70 is a United Electrical Controls Company unit, model 650, and is sensitive to changes in temperature in increments of 1° F. Therefore, when the sterilizer chamber interior is 1° F or more below the pre-set temperature of the indicating recorder controller 70, the controller 70, which is electrically connected to solenoid valve 42, actuates solenoid valve 42 to open the valve and to provide high-pressure steam into the jacket 12 through conduit 38.

The valve 42 is left open as steam is being admitted to the sterilizer jacket 12 (and, through control valve 54, to the sterilizer chamber 10) until the controller 70 senses that the temperature of the chamber 10 has reached the predetermined setting, at which time the controller 70 actuates solenoid valve 42 to close valve 42, thereby to discontinue the introduction of high pressure steam into jacket 12. At such time as the temperature of the sterilizer chamber is approximately 1° F or more below the predetermined setting for the sterilizer chamber, controller 70 would sense this change, provide a signal to re-open solenoid valve 42 to provide additional high pressure steam to the jacket, and thereby to the sterilizer chamber, for the purpose of maintaining the predetermined temperature of the sterilizer chamber. In this way, the temperature of the sterilizer chamber can be maintained relatively constant, often within one degree fluctuations, in order to insure that the minimum temperature necessary to maintain sterilization is achieved.

The use of the indicating recorder controller 70 to actuate the solenoid valve provides one of the important advantages of this invention. The indicating recorder controller 70 can be set at numerous settings, such as in 1° F increments, between the predetermined limits, most desirably between 212° and 275° F and particularly between 250° and 270° F. Therefore, the use of the indicating recorder controller 70 controlling the solenoid valve 42, when the jacket 12 is in fluid communication with the sterilizer chamber 10 during sterilization, allows a single setting to assure a variable, predetermined temperature within the sterilizer chamber 10, and allows setting sterilizer temperature at any desired level subject only to the accuracy of the indicating recorder controller 70. This is important because operating personnel at different laboratories and hospitals have different opinions about the proper sterilization temperatures to be used to sterilize certain items. For example, when sterilizing soft goods, such as operating room garments, bed sheets, pillow cases, hospital gowns, curtains, other linen and the like, some hospital personnel believe that sterilization at too high temperatures damages the fabric, and prefer to sterilize those items at, say, 261° F. Some persons do not believe that high temperature sterilization damages fabrics. The latter persons prefer to sterilize soft goods at higher temperatures, for example, at 270° F. This is a very important judgment question from the standpoint of the time of use of the sterilizer, because there is a logarithmic relationship between sterilizing temperature and the time required to achieve sterilization. For example, sterilization of a batch of soft goods at 250° F might require 10 minutes of sterilization time, whereas at 275° F might take only one minute. Therefore, the ability to set the chamber temperature at a predetermined and variable level is quite important, because it affects the throughput of the sterilizer.

The connection, through valve 54, between the jacket 12 and sterilizer chamber 10 assures that the jacket and chamber are always maintained at substantially the same pressure and therefore temperature, thereby providing a substantially uniform sterilizing temperature throughout the sterilizing chamber and assuring the maximum likelihood of complete sterilization in the minimum period of time, because of lack of substantial variability of temperature within the sterilizing chamber.

Also, when the sterilization cycle is in the exhaust phase, by the closing of chamber valve 54 the pressure in the jacket 12 (which may be a high or low pressure)

is capable of being maintained, thereby pre-heating the chamber 10 and allowing a rapid commencement of pressure build-up for any subsequent sterilizing cycle. This is important, because, in order to reduce sterilizer operating costs, it is desirable to reduce the sterilization cycle time per load to the minimum period, in order to achieve the maximum throughput of articles in the sterilizer, thereby achieving maximum efficiency of sterilizer utilization and minimum cost. Since a sterilizer is an expensive unit, it is preferable to have a single highly efficient sterilizer capable of achieving a high throughput as opposed to plural substantially less efficient sterilizers.

The indicating recorder controller 70, in addition to being interconnected with the solenoid valve 42, is also connected to a timer (not shown) for establishing the time of the sterilizing cycle in such a manner that, if the temperature of the sterilizer chamber 10 drops more than 1° F below the preset temperature for the interior of the chamber 10, the time for the sterilizing cycle is automatically extended to take into account this decrease in temperature. The timer does not, however, start to measure the sterilizing time until the preset sterilizing temperature is reached in chamber 10. The circuitry for accomplishing this resetting of the timer is conventional and will be obvious to those persons having ordinary skill in the art.

As more fully described below, if some "hard goods", such as surgical instruments, laboratory glassware and the like are being sterilized, rapid exhaust of the sterilizer chamber is desirable after completion of sterilization. In order to accomplish this, exhaust solenoid valve 80 is automatically opened, being actuated by the sterilizing cycle timer (not shown) upon completion of the sterilization cycle, to place sterilizer chamber 10 in fluid communication with the solenoid valve 80 of conduit 72. The steam exiting the sterilizer jacket and chamber then passes through check valve 82 and is then introduced into the neck of the ejector 88, which is a venturi-type of injector for admixing cooling water and steam.

The cooling water is introduced at the up-stream mouth of the ejector 88, and steam is introduced at the neck of the ejector in order to provide for complete mixing of the steam with the cooling water. The exhaust from ejector 88 discharges into collecting funnel 92 from which it is discharged to a drain. For safety purposes, it is necessary that the steam exhaust from the sterilizer be cooled to a temperature of 140° F or less. Accordingly, cooling water is provided at a temperature of about 50° to 70° F and at a suitable flow rate for the purpose of achieving of the necessary cooling. The water supply from suitable water source 100 passes through strainer 102 for the purpose of removing any foreign particles, and then passes through manually operable valve 104 which merely controls the flow of cooling water to the ejector. Cooling water then exits manual valve 104 and enters vacuum breaker 106, which is necessary to prevent backflow of water should water supply pressure drop to zero. The cooling water then passes through check valve 108, the purpose of which is to prevent any backflow in the water line, and is then introduced into ejector 88 through either flow control valve 84 or water solenoid valve 86.

Conduit 94 is connected to jacket 12 and to the funnel 92 which discharges to the drain, and includes a steam trap 90, the purpose of which is to remove condensate from the jacket 12.

Flow control valve 84 is opened when the gradual release of steam through the slow exhaust flow control valve 78 is desired, providing a relatively low flow of water through the ejector 88 to accommodate the relatively lower exit flow of steam from the sterilizer. Water solenoid valve 86 is actuated to provide a high flow rate of cooling water when exhaust solenoid valve 80 is opened to provide relatively fast release of steam from the sterilizer.

Flow control valve 78 is a needle valve which bleeds the steam in the sterilizing chamber slowly, desirably over a period of approximately 25 to 30 minutes. This valve is used when sterilizing liquids, to allow the sterilizer to be exhausted sufficiently slowly to prevent rapid volatilization of liquids in glass bottles, thereby to avoid breaking of the bottles.

The solenoid system shown in the lower left-hand corner of FIG. 1 is the control system for operating the actuating cylinders 16 and 124 to open, close and lock in place door 14.

Located peripherally about the front of sterilizer 10 and abutting door 14 in the closed position shown in FIG. 1, is the inflatable seal 22. This seal is located in a recess 20 in the front of the sterilizer. The seal is filled with pressurized air or water from a suitable source of air or water (not shown) at a pressure of about 60 p.s.i.g. Inflatible seals are common in the art and are of well known construction. When the door 14 is in place, the seal 22 is inflated by the operation of solenoid 116, as a result of the actuation of which the seal is provided with high pressure air or water and is inflated to abut tightly the interior face of door 14 to prevent leakage of high pressure steam around the edges of the door. When the sterilization cycle has been completed, and the door is to be opened, solenoid 120 is opened and solenoid 116 is closed to permit the drainage of air or water from the seal 22.

Cylinder and piston assembly 124, 126 functions as a safety device to prevent the accidental dropping of door 14 as a result of failure of cylinder 16. It would be hazardous if the door 14 were accidentally to drop as a result of a failure of the hydraulic cylinder 16 under circumstances when high pressure steam was in the sterilizer chamber 10. Accordingly, the lower edge of door 14 is provided with a dependent flange 128 having an aperature extending horizontally therethrough (not shown). Cylinder 124 is mounted at the bottom of the sterilizing chamber and operates a piston 126, the free end of which operates as a pin which seats in the aperature in flange 128. The piston 126 is spring loaded to the flange engaging position, so that when the door 14 is closed and in the position shown in FIG. 1, the piston is engaged in the aperature in flange 128, and any failure of hydraulic cylinder 16 will not result in a dropping of the door 14. The operation of hydraulic (or pneumatic) cylinder 124 is regulated by solenoid valve 118 to control the flow of hydraulic fluid (or air) in the cylinder to seat and unseat the piston from the aperature in flange 128.

The apparatus of this invention is provided with suitable circuitry, of a type which will be apparent to a person having ordinary skill in the art, for the purpose of interconnecting the various electrical and hydraulic (or pneumatic) controls to operate the sterilizer in a predetermined sequence. The sterilizer unit is desirably provided, above its front face, with a control panel with suitable buttons, dials and indicators. For example, the control panel could contain the two pressure gauges 58 and 60 for indicating jacket pressure and chamber pressure and the temperature recorder controller 70 for indicating the actual temperature within the sterilizer chamber 10 and including an adjustable dial for setting the particular desired chamber temperature.

Two timers would desirably be included on the control panel, each of which would be preset manually. A sterilizing timer would set the time of the actual steam sterilizing (which would be subject to automatic adjustment, each time that the temperature in the sterilizer went below the predetermined minimum temperature by 1° F or more). The second timer would be utilized to establish the drying time, if desired, for drying the sterilizer contents.

The control panel could have suitable pilot light indicators, which could light up to indicate the stage of the cycle that the unit is in, and appropriate light indicators would be provided with the following designations: heat, sterilizing, rapid exhaust (of the chamber), slow exhaust (of the chamber), drying and sterile. It is believed that the foregoing indications are self-explanatory, except that the sterile pilot light indicator would indicate the completion of the selected cycle and the return of the chamber pressure to ambient.

The control panel would also be provided with a suitable on-off switch to turn on the unit, a suitable "heat" switch to commence introduction of steam into the jacket 12 to preheat the unit, and a suitable "close door, start cycle" switch which would commence the actual sterilizing cycle. Additional switches would be provided for "wrap cycle", "unwrap cycle," "liquid cycle" and "streaming steam," to designate the particular cycle selected. After the appropriate cycle is selected, timers set and sterilizing temperature set, the cycles would operate automatically. The latter four cycles are described as follow. The wrap cycle is used for soft goods and includes a drying step after sterilization, whereby upon completion of sterilization the steam is rapidly exhausted from the sterilizer and heating of the sterilizer contents continues (from the steam in jacket 12) after the sterilizer is exhausted to effect the drying. While drying is being accomplished valves 80 and 86 remain open.

The unwrap cycle is used for hard goods other than liquids and includes a rapid exhaust of steam by opening valves 80 and 86 after the steam sterilization is completed. This cycle includes no drying.

The liquid cycle is the same as the unwrap cycle except that valves 78 and 84 are opened to evacuate the steam in the sterilizer more slowly to avoid volatilization of the liquid and the attendant possibility of breaking their glass containers.

The streaming steam cycle is used to sterilize media or animal food, for example, and involves the streaming of low pressure steam through the chamber 10 and immediately evacuating it, during the steam sterilizing operation, by opening valves 80 and 86. This is a fairly lengthy operation, often taking 2 to 3 hours, usually at about 212° F with a very low pressure in chamber 10.

In the operation of the sterilizing apparatus of this invention, the power on-off switch would first be turned on. At this point door 14 would be open from the previous cycle. This would turn on all power for all of the switches and mechanisms of the apparatus. At such time as commencement of operation of the unit is desired, the "heat" button would be pressed, which would open heat solenoid valve 36 to effect the introduction into jacket 12 of steam from a suitable steam source at a preferred pressure of 15 p.s.i. During this period, the chamber solenoid valve 54 is closed, so that the only portion of the unit directly receiving steam is jacket 12.

Some persons prefer to have only a brief period of preheating before commencing sterilizing. Others prefer to commence operation of the sterilizers at the beginning of a work day by commencing the pre-heating of the sterilizer, although sterilization may not be intended to commence for a period of one or more hours. Still other persons prefer to leave the sterilizer in the pre-heat stage at all times when it is not operating and will even leave the sterilizer in the pre-heat stage overnight, when sterilizing is not being done.

At such time as it is desired to sterilize a load, the load would be inserted inside the sterilizer. At this point, prior to commencement of the sterilization cycle, the door 14 is in the open position (not shown).

The sterilizer of this invention is capable of being utilized with all types of laboratory and hospital hard goods, liquids and soft goods. For example, the sterilizer can be utilized to sterilize such soft goods as bed linens, curtains, uniforms, dressing gowns, surgical drapes and the like. Some of these can come pre-packaged in a porous package, in which case it may be desirable to pump any air contained within the package from package prior to the commencement of sterilization.

Among the hard goods which may be sterilized in the unit are glass containers of parenteral solutions. In order to avoid rapid volatilization of these solutions during the exhaust of steam from the sterilizer 10, a slow exhaust operation is provided, utilizing the needle valve 78 and the flow control valve 84.

On the other hand, when other hard goods such as surgical instruments are being sterilized, it is desirable to exhaust steam rapidly from the sterilizing unit after sterilization is complete. In this case the solenoid valve 80 would be used to achieve the rapid exhaust and water solenoid valve 86 would be utilized to provide a high flow rate of cooling water to admix wth the steam in ejector 88 to provide for a safe removal of steam from the sterilizer. The determination of whether a rapid or slow exhaust is to be achieved, is determined by pushing the "liquid cycle" button when a slow exhaust is desired and the "unwrap cycle" when a fast exhaust is desired. The exhaust is then automatically accomplished as part of the process of the sterilizing cycle.

At such time as the equipment to be sterilized is located in the sterilizing chamber and commencement of the sterilizing process is desired, the sterilizing time and temperature are set and the drying time is set (for a wrap cycle). Then the "close door/start cycle" or other suitable button would be pressed, together with the button indicating the particular cycle desired, such as wrap cycle, unwrap cycle, liquid cycle or streaming steam. This would initially actuate solenoid 110 to introduce hydraulic fluid or air to cylinder 16 to move door 14 to the closed position shown in FIG. 1. When the door has moved to the closed position, solenoid 118 is automatically actuated to initiate operation of hydraulic cylinder 124 to displace hydraulic piston 125 so that the piston 126 engages flange 128 to prevent inadvertent displacement downward of door 14.

It is to be noted that door 14 is suitably mounted for up and down movement on rollers in suitable channels, and is restrained thereby from outward movement under the effect of the pressure in sterilizer chamber 10, in a manner which is well known in the art.

When the door has been closed and is locked in place, door seal pressure solenoid valve 116 is automatically actuated to control the introduction into the inflatible seal 22 of a suitable quantity of water or other fluid. When all of these steps are completed, introduction of steam into the sterilizer chamber is ready to commence. In order to prevent premature introduction of steam into the sterilizer chamber, the interrelationship between the various operations is established so that no steam can be introduced until the door is closed, locked in place and the inflatable seal is actuated.

The water or air supply for inflating the seal 22 should be at a pressure of at least 30 p.s.i.g. After the seals 22 have been inflated, a time delay is build into the circuitry for the system in order to insure complete expansion of the seal 22. After that time delay has passed, the sterilizer chamber 10 is charged with steam to displace all air located in the sterilizer chamber.

The initial charging of the sterilizer will depend upon the particular sterilizer temperature desired to be maintained. For purposes of this discussion, it is assumed that a pressure of 15 p.s.i.g. will produce a sterilizer temperature of 250° F. Therefore, if a sterilizer temperature of 250° F is desired to be maintained, the controller 70 would manually be set at that temperature and its initial actuation would open chamber valve 54 to permit steam from jacket 12 to enter the sterilizing chamber itself. Initially, while the chamber is being charged with steam, the air in the chamber is being displaced by the incoming steam and exits through the steam trap 76 from which it goes into the ejector 26 and is mixed with water supply water introduced by the automatic actuation of flow control valve 84 to cool the exiting air and any steam that may be entrained therein to the requisite 140° F maximum temperature. When the interior of the sterilizing unit has reached the predetermined temperature, as sensed by controller 70, pressure regulator 40 would prevent further flow of steam into the sterilizer jacket 12 until the jacket pressure drops below 15 p.s.i.g., it being understood that chamber valve 54 is open at all times during the actual steam sterilization step to maintain complete fluid communication between the jacket 12 and the chamber 10.

If it is desired to maintain a temperature higher than that achieved by the pressure determined by pressure reducing valve 40, jacket solenoid valve 42 would be opened automatically in response to the setting of controller 70 to permit substantially higher pressure steam, preferably at a pressure at a range from about 35 to about 40 p.s.i.g., to be introduced through conduit 38 into jacket 12 and therefrom into the sterilizer chamber 10. Pressure reducing valve 40 shuts off when the downstream pressure exceeds 15 p.s.i.g. so that only one loop of the steam supply system is operating when the valve 42 is open. In either event, whether steam is being supplied at 15 p.s.i.g. or at the higher pressure, the jacket 12 and chamber 10 are in fluid communication during the actual sterilizing portion of the cycle, and the valve 42 is opened or shut in response to indicating recorder controller 70. If the temperature in the chamber is lower than the preset temperature established by controller 70, then controller 70 will open valve 42, to permit the introduction into the jacket 12, and thereby into the sterilizer chamber 10, of sufficient steam to permit the temperature in the chamber to be elevated to the predetermined temperature. When that higher temperature has again been sensed, the controller 70 would then shut off the supply valve. This feature of the invention allows a wide variety of temperature settings to be achieved within a predetermined range, consistent only with the sensitivity of the temperature controller. This facilitates maintaining a uniform temperature throughout the sterilizer chamber, since the jacket and sterilizer chamber are at the same temperature, thereby assuring maximum sterilization results in the minimum periods of time. The indicating recorder controller 70 has a sensor located within the sterilizer chamber for the purpose of sensing the temperature therein.

The sterilizing cycle then continues at the predetermined temperature, which is maintained fairly accurately within approximately 1° F because of the sensitivity of the temperature controller 70 until the predetermined time period for the sterilizing portion of the cycle has been completed. As noted above, the timer for the sterilizing operation is so set that, if the temperature drops below the predetermined temperature by 1° F or more, the time of sterilization is adjusted accordingly.

When the sterilizing temperature has been maintained for the predetermined period of time valve 54 is automatically closed and the sterilizer chamber 10 may then be rapidly or slowly exhausted depending upon the contents being sterilized. If "hard goods" other than liquids or "soft goods" are being sterilized, once the sterilization temperature and time has been satisfied, it is desirable quickly to evacuate the sterilizing chamber, to facilitate the prompt removal of the contents and the reuse of the sterilizer for a subsequent batch of materials. On the other hand, if liquids in glass bottles are being sterilized, it is necessary gradually to evacuate and cool the interior of the sterilizer chamber in order to prevent rapid temperature change which could volatilize the liquid and break or explode the bottles.

Accordingly, if "hard goods" other than liquids or "soft goods" have been sterilized, upon completion of the time necessary to effect sterilization, jacket control valve 42 is closed, chamber valve 54 is also closed, and exhaust solenoid valve 80 and water solenoid valve 86 are opened to permit a rapid exhaust of steam from the sterilizer to exhaust line 74 and into ejector 88, where the high pressure and high temperature steam is admixed with a high volume of relatively low temperature water in order to lower the temperature of the admixture to 140° F or less before it is delivered from the sterilizer unit to a suitable drain.

In the event that liquids have been sterilized, it is desired to evacuate the sterilizer chamber more slowly, solenoid exhaust valve 80 is permitted to remain closed (after valves 42 and 54 have been closed) and flow control valve 78 is opened at the time that flow control 84 is opened. Needle valve 78 permits a bleeding of the steam from the sterilizing chamber over a period of 25 to 30 minutes, and the valve 84 allows a lower flow rate of cooling water into ejector 88 to admix with the steam from the sterilizing chamber and jacket.

If "soft goods" are being sterilized, it is desirable to dry the soft goods before emptying the sterilizer. For this purpose, the sterilizer is rapidly exhausted by opening exhaust solenoid valve 80 and flow control valve 86 in the same manner as is accomplished when hard goods are being sterilized. When the exhausting has been completed, so that a pressure within the sterilizing chamber of about 28 inches of mercury is reached, virtually all of the steam has been exhausted from the sterilizing chamber and a vacuum exists in the sterilizing chamber. At that point, valves 80 and 86 are allowed to remain open during an additional period of 25 to 30 minutes (which may be varied if desired) to permit drying of the soft goods in the sterilizing chamber by the continued introduction of low pressure steam into the jacket 12.

When the drying and/or exhausting at the chamber has been completed, valves 80 and 86 are automatically closed and air admission valve 50 is automatically opened, to permit the introduction of air into the interior of the sterilizer chamber. When the interior of the chamber has reached ambient pressure, door seal vent solenoid valve 120 is automatically actuated to vent the door seal. At the same time, door safety lock solenoid valve 118 is automatically actuated to retract piston 126. At that point, a light on the unit (not shown) would light up and buzzer (also not shown) would sound so that the operator would know that the sterilizing cycle has been completed. A separate manually operated button would then be operated to open door valve 114 by the actuation of solenoid valve 112 to retract the door to the open position for access to the contents of the sterilizer.

When sterilizing "soft goods" it is often necessary to accelerate the removal of entrapped air in packs that are wrapped in fabric, prior to commencement of the actual sterilization. To accomplish this, several cycles of alternatively pressuring and evacuating the sterilizer chamber are used to "pump" the air out of the pack. The conventional method of achieving a vacuum in the chamber 10 as part of this "pumping" process is to use a water ring vacuum pump, which is quite expensive. For general purpose and laboratory use, the vacuum capable of being created by the use of an ejector alone, as by use of the ejector 88 shown in FIG. 1, with solenoid valve 86 open to create a substantially high flow rate through the ejector, is sufficient to create an adequate vacuum in the sterilizing chamber. In that event, after the vacuum has been produced, valves 80 and 86 would be closed and additional steam introduced through valve 54 to "pump" out the air entrained within the packs of soft goods. This cycle would be repeated several times.

Figure 4:
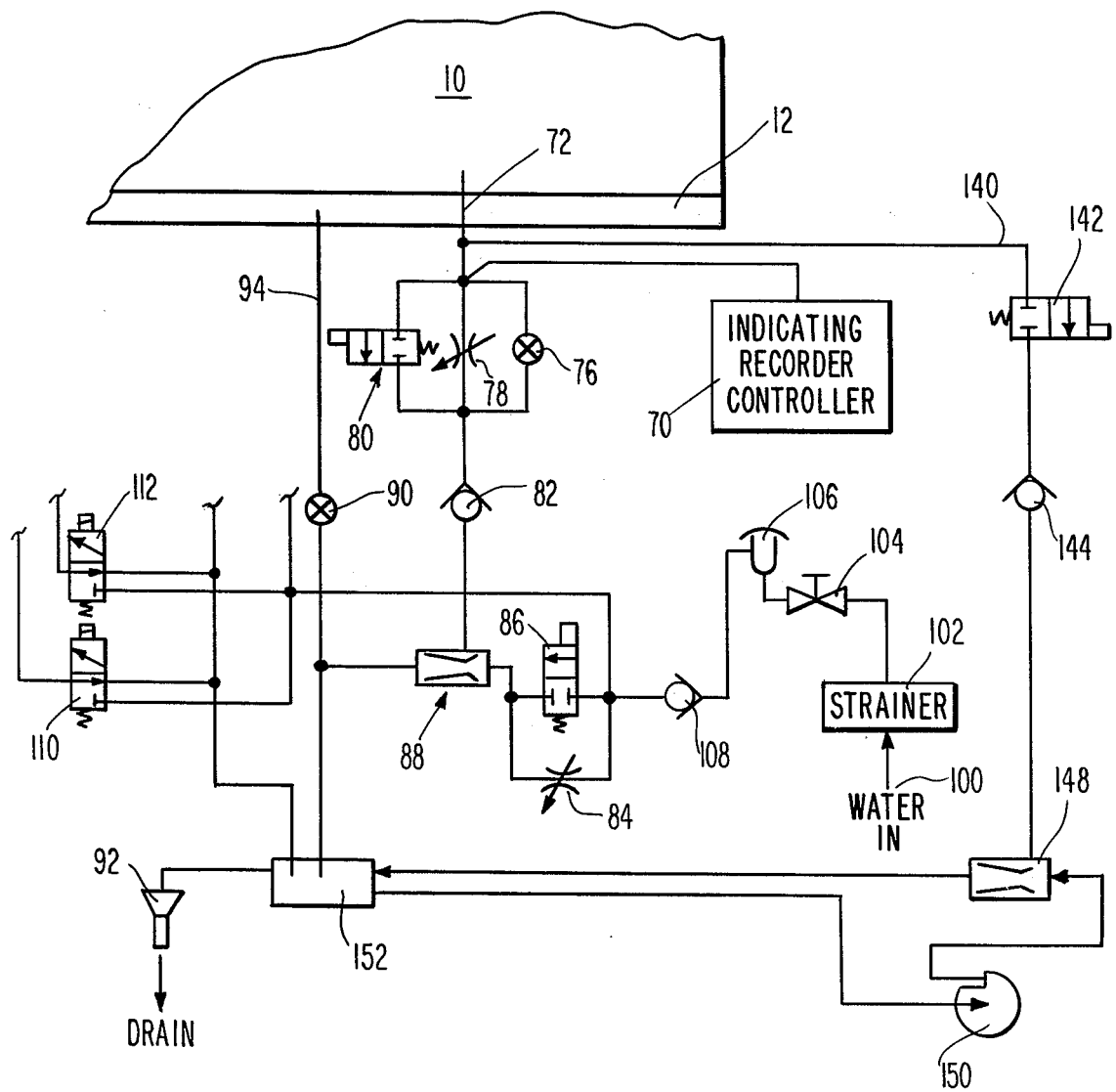
FIG. 4 is a view similar to FIG. 1 illustrating the additional equipment utilized to achieve high vacuum exhaust of the sterilizer interior.

If it is desired to speed the productivity of the sterilizer, a high vacuum would be necessary. This is often desired, since the evacuation time can occupy approximately half of the time of the entire sterilization cycle. A modification of the embodiment of the invention shown in FIG. 1 is illustrated in FIG. 4 for the purpose of providing the high rate of evacuation desired. This system, as seen in FIG. 4, is connected at one end to chamber evacuation conduit 72 and at the other end into a reservoir 152 which empties into drain 92. The purpose of this reservoir 152 is to collect the water used in the high vacuum system and to allow it to be recycled. The high vacuum system includes exhaust solenoid valve 142, check valve 144, ejector 148, reservoir 152 and pump 150. Pump 150 is a high pressure (such as 100 p.s.i.g.) turbine pump. The reservoir 152 is provided so that the pump water can be recirculated to reduce the amount of water required for the evacuating function. In order to reduce the temperature, service water is utilized when the ejector is in operation. Rather than waste the energy of the service water from source 100, it is introduced through a small ejector 88 to reservoir 152. This use of service water increases pump performance by approximately 25 percent beyond that which would be achieved if ejector 148 would be used with pump 150 and without additional water introduced.

The process of the invention therefore comprises the steps of pre-heating the sterilizer jacket, introducing the objects to be sterilized into the sterilizer chamber, closing and locking the chamber door and inflating the door seal, introducing steam from the jacket into the sterilizer chamber, sensing on a continuous basis the temperature in the sterilizer chamber, while maintaining continuous steam communication between the jacket and chamber, and selectively controlling the introduction of steam into the jacket in response to the temperature of the sterilizer chamber.

The preferred embodiments of the invention have been disclosed herein. It will be appreciated that substantial changes in the details of the design and operation of the apparatus and process of the invention can be made without departing from the spirit and scope of the invention.

What is claimed is:
1. A sterilizing apparatus comprising:
   (a) A sterilizing chamber having an open front, a back, and sides;
   (b) A closed jacket encompassing said sides and permitting the circulation of steam peripherally about said sides;
   (c) Door means mounted to said chamber and adapted sealingly to close the front of said chamber;
   (e) First means interconnecting said jacket and said chamber for fluid communication and including first valve means for opening and closing said fluid communication;
   (f) Second means automatically to open said first valve means at the commencement of the sterilizing in said chamber and closing said first valve means at the end of said sterilizing;
   (g) Third means, including a low pressure line and a relatively high pressure line, connected in parallel with each other, connected to said jacket to supply steam to said jacket at two different pressures;
   (h) Second valve means mounted in said high pressure line for controlling flow of steam therethrough; and
   (i) Temperature sensitive means responsive to the temperature in said chamber and actuating said second valve means to supply steam at the relatively high pressure to said jacket until a predetermined temperature is reached and then closing said second valve means, and subsequently actuating said second valve means in response to a subsequent reduction in the temperature in said chamber.

2. Apparatus as set forth in claim 1, wherein said temperature sensitive means includes means sensitive to temperature drops of about 1° F and is adjustable in increments of about 1° F.

3. Apparatus as set forth in claim 1, including adjustable timer means connected to said steam supply means to regulate the supply of steam for an adjustable, predetermined period of time, said timer means being responsive to said temperature sensitive means to increase the time of said cycle in response to a decrease in the temperature of said chamber.

4. Apparatus as set forth in claim 1, including outlet means connected to said chamber to permit evacuation of steam therefrom, and high pressure vacuum pump means connected to said outlet means to create a rapid and substantial vacuum in said chamber.

5. Apparatus as set forth in claim 4, wherein said vacuum pump means comprises a turbine pump and a venturi-type ejector connected in series.

* * * * *